United States Patent
Ultchin et al.

(10) Patent No.: US 11,559,351 B2
(45) Date of Patent: Jan. 24, 2023

(54) TEMPERATURE SENSOR STRUCTURE IN PRINTED-CIRCUIT-BOARD (PCB) WALL OF RADIOFREQUENCY (RF) ABLATION CATHETER TIP ELECTRODE

(71) Applicant: BIOSENSE WEBSTER (ISRAEL) LTD., Yokneam (IL)

(72) Inventors: Yigal Ultchin, Rehovot (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 712 days.

(21) Appl. No.: 16/288,807

(22) Filed: Feb. 28, 2019

(65) Prior Publication Data

US 2020/0275892 A1    Sep. 3, 2020

(51) Int. Cl.
| | |
|---|---|
| *A61B 18/14* | (2006.01) |
| *A61B 5/01* | (2006.01) |
| *A61B 5/00* | (2006.01) |
| *A61B 18/00* | (2006.01) |

(52) U.S. Cl.
CPC ............ *A61B 18/1492* (2013.01); *A61B 5/01* (2013.01); *A61B 5/6852* (2013.01); *A61B 2018/00791* (2013.01); *A61B 2562/12* (2013.01); *A61B 2562/166* (2013.01)

(58) Field of Classification Search
CPC ...... A61B 18/1492; A61B 2018/00714; A61B 5/01; A61B 2562/162; A61B 2562/164; A61B 2562/0271; A61B 2018/00791; A61B 2018/00797; A61B 2018/00803; A61B 2018/00815; A61B 2018/0021
See application file for complete search history.

(56) References Cited

U.S. PATENT DOCUMENTS

| | | | |
|---|---|---|---|
| 2006/0173449 A1* | 8/2006 | Sharareh | A61B 18/1492 606/41 |
| 2007/0219551 A1 | 9/2007 | Honour et al. | |
| 2011/0013669 A1* | 1/2011 | Raj | G01K 1/08 374/179 |
| 2012/0071870 A1 | 3/2012 | Salahieh et al. | |
| 2015/0018818 A1 | 1/2015 | Willard | |
| 2015/0297292 A1* | 10/2015 | Sutermeister | A61B 18/1492 606/41 |
| 2016/0270732 A1* | 9/2016 | Kallback | A61B 5/6852 |
| 2017/0188942 A1 | 7/2017 | Ghaffari et al. | |

FOREIGN PATENT DOCUMENTS

WO    WO2016130713 A1    8/2016

OTHER PUBLICATIONS

European Search Report for corresponding EPA No. 20159814.1 dated Aug. 12, 2020.

* cited by examiner

*Primary Examiner* — Eun Hwa Kim
(74) *Attorney, Agent, or Firm* — Dergosits & Noah LLP; Todd A. Noah

(57) ABSTRACT

A tip electrode of a catheter includes an outer wall and a temperature sensor assembly. The outer wall includes a thermally conductive multilayer printed circuit board (TCM-PCB) that includes a void. The temperature sensor assembly, which is fitted in the void of the TCM-PCB, includes a temperature sensor, one or more thermally insulating layers that surround a volume of the temperature sensor excluding one facet of the volume, and a heat conductive layer covering the excluded facet.

8 Claims, 2 Drawing Sheets

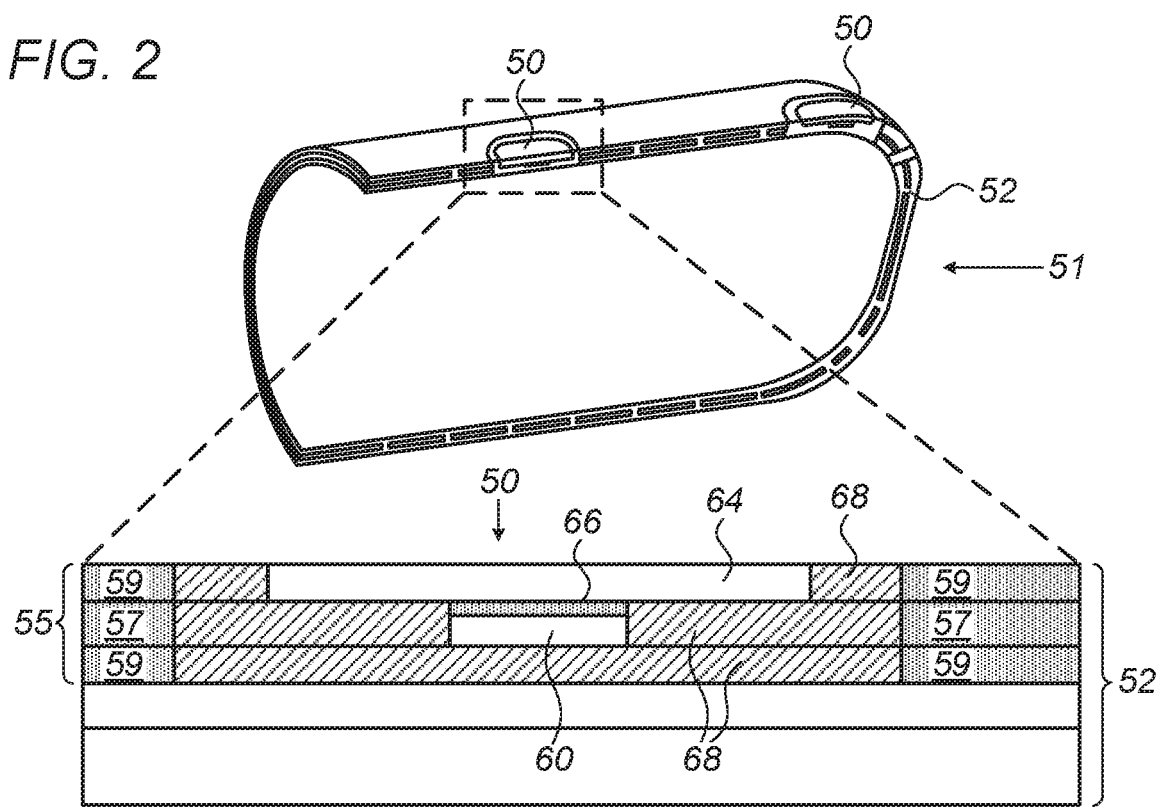
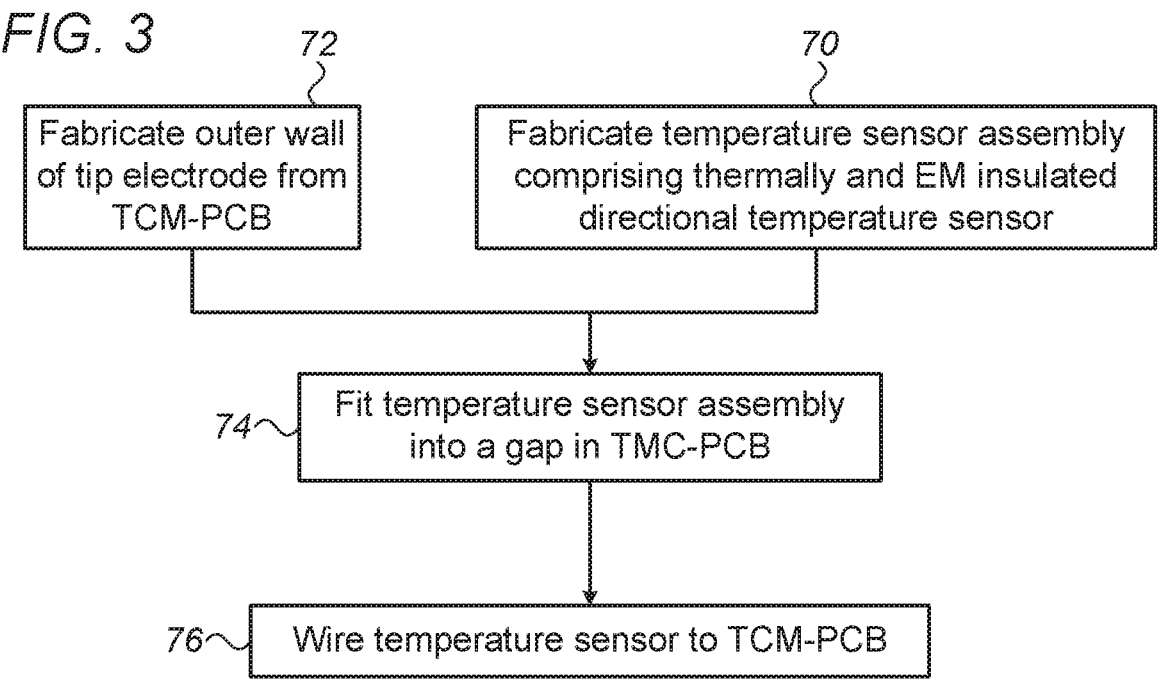

TEMPERATURE SENSOR STRUCTURE IN PRINTED-CIRCUIT-BOARD (PCB) WALL OF RADIOFREQUENCY (RF) ABLATION CATHETER TIP ELECTRODE

FIELD OF THE INVENTION

The present invention relates generally to medical probes, and particularly to radiofrequency (RF) ablation catheters.

BACKGROUND OF THE INVENTION

Temperature sensors incorporated in catheters were previously described in the patent literature. For example, U.S. Patent Application Publication 2012/0071870 describes a tissue electrode assembly including a flexible circuit positioned on a surface of an expandable membrane and comprising at least one base substrate layer, at least one insulating layer and at least one planar conducting layer. An electrically-conductive electrode covers at least a portion of the flexible circuit and a portion of the surface of the membrane not covered by the flexible circuit, wherein the electrically-conductive electrode is foldable upon itself with the membrane to a delivery conformation having a diameter suitable for minimally-invasive delivery of the assembly to the patient. In some embodiments, a number of temperature sensors is incorporated with the electrode assembly.

As another example, U.S. Patent Application Publication 2017/0188942 describes devices and methods that integrate stretchable or flexible circuitry, including arrays of active devices for enhanced sensing, diagnostic, and therapeutic capabilities. The devices may be mounted on a catheter. The invention enables conformal sensing contact with tissues of interest, such as the inner wall of a lumen, a nerve bundle, or the surface of the heart. Such direct, conformal contact increases accuracy of measurement and delivery of therapy. The devices may include temperature sensors.

U.S. Patent Application Publication 2007/0219551 describes a catheter or lead having a flexible printed circuit for conveying signals and/or energy. Each trace may be in electrical connection with one or more external electrical contacts. More specifically, each trace is typically electrically connected to a single contact. The traces and contacts may assist in diagnosis and/or detection of bio-electrical signals emitted by organs, and may transmit such signals to a connector or diagnostic device affixed to the catheter. The external electrical contacts may detect bioelectric energy or may deliver electrical or thermal energy to a target site. The electrical contacts may convey signals from temperature sensing elements.

SUMMARY OF THE INVENTION

An embodiment of the present invention provides a tip electrode of a catheter including an outer wall and a temperature sensor assembly. The outer wall includes a thermally conductive multilayer printed circuit board (TCM-PCB) that includes a void. The temperature sensor assembly, which is fitted in the void of the TCM-PCB, includes a temperature sensor, one or more thermally insulating layers that surround a volume of the temperature sensor excluding one facet of the volume, and a heat conductive layer covering the excluded facet.

In some embodiments, the thermally insulating layers and the temperature sensor are co-packaged.

In some embodiments, the thermally insulating layers are also electromagnetically insulating, and including an additional electromagnetically insulating layer that is disposed over the excluded facet of the temperature sensor.

In an embodiment, the thermally insulating layers are electromagnetically insulating, and the heat conductive layer covering the excluded facet is electromagnetically insulating. In another embodiment, the outer wall is configured for performing radiofrequency ablation.

In some embodiments, the TCM-PCB includes a triple layer PCB including a metal on insulating-substrate on metal layer stack.

In some embodiments, the temperature sensor assembly is curved.

There is additionally provided, in accordance with an embodiment of the present invention, a method for manufacturing tip electrode of a catheter, the method including forming an outer wall of the tip electrode, wherein the outer wall includes a thermally conductive multilayer printed circuit board (TCM-PCB) that includes a void. A temperature sensor assembly is fitted in the void of the TCM-PCB, the temperature sensor assembly including a temperature sensor, one or more thermally insulating layers that surround a volume of the temperature sensor excluding one facet of the volume, and a heat conductive layer covering the excluded facet.

The present invention will be more fully understood from the following detailed description of the embodiments thereof, taken together with the drawings in which:

BRIEF DESCRIPTION OF THE DRAWINGS

FIG. 2 is a schematic, pictorial illustration of the thermally and EM insulated temperature sensor assemblies of FIG. 1, in accordance with embodiments of the present invention; and FIG. 3. is a flow chart that schematically describes a manufacturing method of the catheter tip electrode of FIG. 2, in accordance with an embodiment of the present invention.

DETAILED DESCRIPTION OF EMBODIMENTS

Overview

Figure 1:
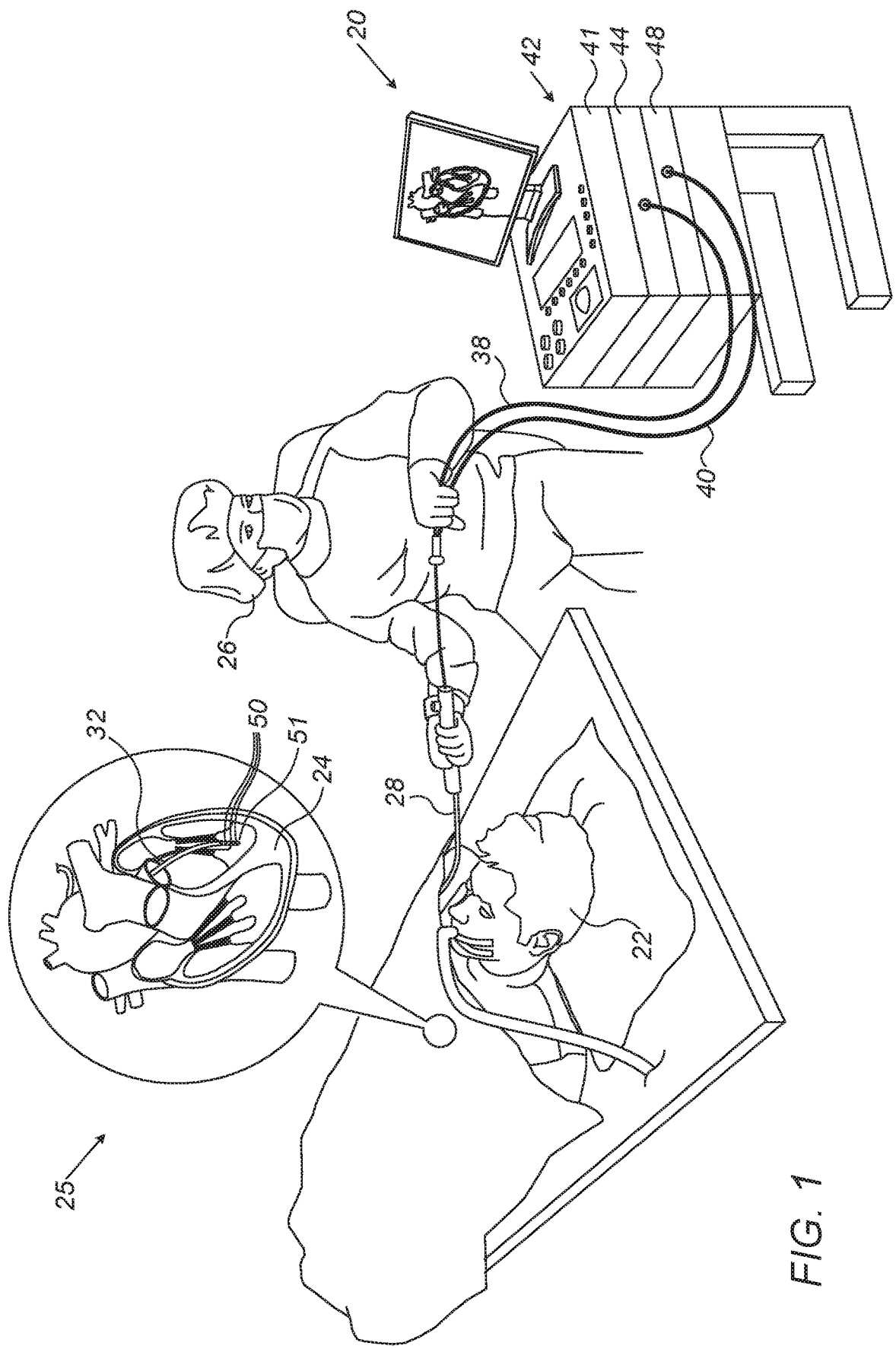
FIG. 1 is a schematic, pictorial illustration of a system for cardiac radiofrequency (RF) ablation therapy comprising a catheter electrode tip fitted with thermally and electromagnetically (EM) insulated temperature sensors, in accordance with an embodiment of the present invention.

Radiofrequency (RF) ablation may be performed using focal catheters comprising a tip electrode. The tip electrode allows the ablation of tissue along a curve, where a physician repeatedly repositions the tip electrode across the curved tissue. During ablation, sensors disposed over the catheter tip may acquire information, such as tissue temperature and contact force. A tip electrode made of a printed circuit board (PCB) may enable easier integration of the tip electrode with additional electrical devices, such as various sensors.

To evacuate excessive heat produced by RF ablation in tissue near the tip electrode, an electrode with a PCB tip may require metal layers on outer and inner surfaces of the PCB. As a result, a temperature measured by a temperature sensor integrated into the tip may be influenced by the temperature of the metalized PCB, and thus deviate from the desired tissue temperature.

Embodiments of the present invention that are described hereinafter provide a thermally and electromagnetically (EM) insulated temperature sensor that is formed (e.g., fitted or fabricated) in a void in a thermally conductive multilayer PCB (TCM-PCB) walled electrode tip. The temperature sensor is configured to measure temperature of tissue in a direction away from the electrode tip (e.g., a direction largely normal to a local surface of the tip).

In the context of this description the term "electromagnetically insulating layers" means that the layer considerably attenuates static or time-dependent electromagnetic fields, such as those generated by the catheter tip electrode, or by other devices, that would otherwise penetrate into a volume fully surrounded by the electromagnetically insulating layers.

In some embodiments, the disclosed TCM-PCB comprises a triple layer PCB comprising metal/insulating-substrate/metal layers, as described below. The temperature sensor (which could be a thermocouple or a thermistor) is formed in the triple layer and is surrounded by a thermally and EM insulating material, except in an outward direction largely normal to the surface of the triple layer.

In the outward direction, a heat conductive path (that is nevertheless EM insulating) is formed, for example, by overlaying the temperature sensor with a thin electrical insulator layer topped by a thermally and electrically conducting layer. Another option to produce such a path is to overlay the temperature sensor with a thermally conductive EM insulating layer, made of, for example, carbon-based material. With either configuration, the temperature measured by the sensor is mainly influenced by the heat of the tissue undergoing RF ablation, not by the temperature of nearby PCB. Furthermore, the EM insulation acts to reduce electromagnetic noise pickup by the temperature sensor, especially for a thermocouple type of temperature sensor.

In some embodiments, the thermally insulating layers and the temperature sensor are co-packaged before being fitted as a single assembly into a void in the TCM-PCB. In other embodiments, the thermally insulating layers and the temperature sensor are fitted separately by, for example, first forming the insulating layers and afterwards installing the temperature sensor.

The disclosed solution thermally insulates the temperature sensor from the catheter tip, while leaving a thermal path between the temperature sensor and the outside. In this manner, the internal heat flow from the catheter tip to the sensor is kept to a minimum, and maximum correlation is achieved between the measurement and tissue temperature.

By enabling better temperature monitoring, the disclosed thermally and EM insulated temperature sensor can substantially improve the measurement of tissue temperature during RF ablation, and thereby minimize clinical side effects, such as collateral thermal damage to nearby tissue caused by, for example, overheating.

System Description

FIG. 1 is a schematic, pictorial illustration of a system for cardiac radiofrequency (RF) ablation therapy comprising a catheter 28 tip electrode tip 51 fitted with thermally and electromagnetically (EM) insulated temperature sensors, in accordance with an embodiment of the present invention. Tip electrode 51 of catheter 28, seen in inset 25, comprises one or more of the disclosed thermally insulated temperature sensor assemblies 50.

An operator 26 inserts catheter 28 through a blood vessel into a chamber of a heart 24 of a subject 22, and manipulates the catheter such that a distal end 32 of the catheter contacts the endocardium in an area that is to be treated. After positioning distal end 32 at an ablation site, and ensuring that the tip is in contact with the endocardium, operator 26 actuates an RF energy generator 44 in a control console 42 to supply RF energy via a cable 38 to distal end 32.

During ablation, an irrigation pump 48 supplies catheter 28 distal end 32 with cooling fluid, such as normal saline solution, via a tube 40 and a lumen in catheter 28. Operation of the RF energy generator and the irrigation pump may be coordinated in order to give the appropriate volume of irrigation during ablation, so as to cool the tip of the catheter and the tissue without overloading the heart with irrigation fluid. Each thermally insulated temperature sensor inside assembly 50 provides feedback to console 42 for use, for example, in controlling the RF energy dosage and/or irrigation volume.

Although the pictured embodiment describes specifically the use of a catheter comprising a single RF ablation electrode tip, the technique described herein may be applied in ablation catheters comprising multiple PCB-made electrodes, with each electrode comprising the disclosed thermally insulated temperature sensor assemblies 50.

Temperature Sensor Structure in PCB Wall of RF Ablation Catheter Tip Electrode

FIG. 2 is a schematic, pictorial illustration of the thermally and EM insulated temperature sensor assemblies 50 of FIG. 1, in accordance with embodiments of the present invention. As seen, catheter tip electrode 51 comprises several temperature sensor assemblies 50 which may also be formed in spherically-curved regions of a TCM-PCB 52 portion of tip electrode 51. Each of the temperature sensor assemblies 50 includes a temperature sensor 60, which is typically a thermocouple or a thermistor.

Sensor 60 is embedded in thermoplastic layers 68 of TCM-PCB 52, such as layers comprising polyether-etherketone (PEEK) or polyurethane (PU). Layers 68 interrupt (e.g., are fitted within a void of) multilayer PCB wall 55 of tip electrode 51, which is typically made of a polymer laminate substrate layer 57 between outer and inner metal layers 59.

In the embodiment seen, a thermally conductive layer 64 covers an excluded facet (i.e., a facet not covered by a layer 68) of sensor 60, thereby creating a directional or collimated thermal channel for sensor 60 to sense temperature. As seen, this direction is largely outwardly normal to the local surface of electrode tip 51. Thermally conductive layer 64 may be made of metal or be based on carbon.

In an embodiment, layers 68 are thermally and electrically insulating, being made, for example, by at least one of PEEK, Polyimide, and PU or any material of similar electrical and thermal properties. Layer 64 is thermally and electrically conductive (e.g., gold electrode). A thin electromagnetically insulating layer 66, such as a thin sheet of PU, is put on top of the excluded facet of sensor 60, so as to complete electromagnetic insulation of sensor 60. Layer 66 does not impede the heat flow due to its thinness relative to the scale of the sensor structure.

The example illustration shown in FIG. 2 is chosen purely for the sake of conceptual clarity. Other possibilities to integrate (e.g., fit) temperature sensor 60 into wall 55 exist, such using the same material for layers 57 and 68.

FIG. 3. is a flow chart that schematically describes a manufacturing method of the catheter tip electrode of FIG. 2, in accordance with an embodiment of the present invention. The process begins with fabricating wall 55 of catheter tip electrode 51 from TCM-PCB 52, at a catheter tip electrode wall manufacturing step 70. Step 70 comprises forming gaps in wall 55 in preparation for fitting temperature sensors in wall 55. In parallel, at a temperature sensor assembly manufacturing step 72, temperature sensor assembly 50, comprising sensor 60, is fabricated. At an integration step 74, assembly 50 is fitted into wall 55, to form the structure shown in FIG. 2. Finally, sensor 60 is wired (e.g., soldered to form electrical leads) to TCM-PCB 52.

The flow chart described by FIG. 3 is highly simplified, and shows only elements relevant to one possible embodiment of the invention. Other manufacturing methods, for example those in which sensor 60 is fitted to wall 55 in a different manner, may occur to a person skilled in the art, after reading this description.

Although the embodiments described herein mainly address design and manufacturing of catheter parts, the temperature assembly sensor described herein can also be used in other medical and non-medical PCB based devices.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A tip electrode of a catheter, the tip electrode comprising:
    a thermally conductive multilayer printed circuit board (TCM-PCB) defining an outer wall of the tip electrode; and
    a temperature sensor assembly formed in a gap within the TCM-PCB, the temperature sensor assembly comprising:
        a plurality of thermally and electrically insulating layers having an outermost layer of the plurality of thermally and electrically insulating layers defining a top surface;
        a thermal channel formed through the plurality of thermally and electrically insulating layers defined by an innermost layer of the plurality of thermally and electrically insulating layers;
        a temperature sensor embedded in the thermal channel and disposed on a top surface of the innermost layer of the plurality of thermally and electrically insulating layers, the temperature sensor having a top surface not covered by the plurality of thermally and electrically insulating layers;
        an electromagnetically insulating layer formed on the top surface of the temperature sensor, the electromagnetically insulating layer being configured to allow heat conduction through the thermal channel to the temperature sensor; and
        a heat conductive layer covering the electromagnetically insulating layer.

2. The tip electrode according to claim 1, wherein the outer wall of the TCM-PCB is configured for performing radiofrequency ablation.

3. The tip electrode according to claim 1, wherein the TCM-PCB comprises a triple layer printed circuit board (PCB) comprising a metal on insulating substrate on metal layer stack.

4. The tip electrode according to claim 1, wherein the temperature sensor assembly is curved.

5. A method for manufacturing tip electrode of a catheter, the method comprising:
    forming an outer wall of the tip electrode, wherein the outer wall comprises a multilayer printed circuit board (TCM-PCB);
    forming a gap within the TCM-PCB;
    forming a temperature sensor assembly configured for fitting in the gap, the temperature sensor assembly comprising:
        a plurality of thermally and electrically insulating layers having an outermost layer of the plurality of thermally and electrically insulating layers defining a top surface,
        a thermal channel formed through the plurality of thermally and electrically insulating layers and defined in part by an innermost layer of the plurality of thermally and electrically insulating layers,
        a temperature sensor embedded in the thermal channel and disposed on a top surface of the innermost layer of the plurality of thermally and electrically insulating layers, the temperature sensor having a top surface not covered by the plurality of thermally and electrically insulating layers,
        an electromagnetically insulating layer formed on the top surface of the temperature sensor, the electromagnetically insulating layer being configured to allow heat conduction through the thermal channel to the temperature sensor, and
        a heat conductive layer covering the electromagnetically insulating layer; and
    fitting the temperature sensor assembly in the gap of the TCM-PCB.

6. The manufacturing method according to claim 5, wherein the outer wall of the TCM-PCB is configured for performing radiofrequency ablation.

7. The manufacturing method according to claim 5, wherein the TCM-PCB comprises a triple layer printed circuit board (PCB) comprising a metal on insulating substrate on metal layer stack.

8. The manufacturing method according to claim 5, wherein fitting the temperature sensor assembly comprises fitting a curved temperature sensor assembly.

* * * * *